(12) United States Patent
Scheller et al.

(10) Patent No.: US 10,646,113 B2
(45) Date of Patent: May 12, 2020

(54) ILLUMINATED CANNULA

(71) Applicant: Katalyst Surgical, LLC, Chesterfield, MO (US)

(72) Inventors: Gregg D Scheller, Wildwood, MO (US); Daniel J Wiener, St. Charles, MO (US); Daniel J Wall, Hazelwood, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 278 days.

(21) Appl. No.: 15/676,370

(22) Filed: Aug. 14, 2017

(65) Prior Publication Data
US 2018/0070808 A1    Mar. 15, 2018

Related U.S. Application Data

(60) Provisional application No. 62/385,741, filed on Sep. 9, 2016.

(51) Int. Cl.
*A61B 1/313* (2006.01)
*A61B 3/00* (2006.01)
(Continued)

(52) U.S. Cl.
CPC ............ *A61B 1/313* (2013.01); *A61B 1/0011* (2013.01); *A61B 1/015* (2013.01); *A61B 1/07* (2013.01);
(Continued)

(58) Field of Classification Search
CPC ............ A61B 17/3417; A61B 17/3462; A61B 17/3421; A61B 1/313; A61B 1/07;
(Continued)

(56) References Cited

U.S. PATENT DOCUMENTS 3,174,851 A    3/1965   Buehler et al.
4,122,853 A    10/1978  Smith
(Continued)

FOREIGN PATENT DOCUMENTS

EP    0900547 B1    3/1999
GB    2208805 A     4/1989
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — David W Bates
*Assistant Examiner* — Marcela I Shirsat

(57) ABSTRACT

An illuminated cannula may include an illumination tube, a hub, a cannula base, a valve, an illumination source connector, an optic fiber, and an optic fiber guide. The valve may be disposed in the cannula base. The cannula base may be fixed to the hub. The hub may include a hub aperture. The illumination tube may be disposed in the cannula base. The optic fiber guide may be disposed in the hub. The optic fiber may be disposed in the illumination source connector, the hub, the optic fiber guide, and the cannula base. The optic fiber may be optically coupled to the illumination tube. Illumination light from an illumination source may be configured to transmit through the optic fiber and into the illumination tube.

16 Claims, 12 Drawing Sheets

(51) Int. Cl.
- *A61B 1/07* (2006.01)
- *A61B 1/00* (2006.01)
- *A61F 9/007* (2006.01)
- *A61B 1/015* (2006.01)
- *A61B 90/30* (2016.01)

(52) U.S. Cl.
CPC ............ *A61B 3/0008* (2013.01); *A61B 90/30* (2016.02); *A61F 9/007* (2013.01); *A61B 2090/306* (2016.02)

(58) Field of Classification Search
CPC ..... A61B 1/06; A61B 90/30; A61B 2090/306; A61B 3/0008; A61F 9/007; A61M 39/0247; A61M 25/02; A61M 25/0606; A61M 2039/0633
USPC ................. 600/249, 199, 212, 203, 223; 604/164.01, 164.11, 167.03, 167.04, 604/174–175
See application file for complete search history.

(56) References Cited

U.S. PATENT DOCUMENTS

| | | | |
|---|---|---|---|
| 4,147,443 A | 4/1979 | Skobel | |
| 4,222,375 A * | 9/1980 | Martinez | A61B 1/07 600/249 |
| 4,402,681 A * | 9/1983 | Haas | A61F 9/00781 604/175 |
| 4,687,293 A | 8/1987 | Randazzo | |
| 4,744,360 A | 5/1988 | Bath | |
| 4,870,952 A * | 10/1989 | Martinez | A61B 1/00117 362/572 |
| 5,190,050 A | 3/1993 | Nitzsche | |
| 5,228,852 A | 7/1993 | Goldsmith et al. | |
| 5,257,988 A | 11/1993 | L'Esperance, Jr. | |
| 5,322,055 A | 6/1994 | Davison et al. | |
| 5,322,064 A | 6/1994 | Lundquist | |
| 5,346,504 A | 9/1994 | Ortiz et al. | |
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,735,842 A | 4/1998 | Kruege et al. | |
| 5,855,577 A | 1/1999 | Murphy-Chutorian et al. | |
| 5,873,865 A | 2/1999 | Horzewski et al. | |
| 5,951,544 A | 9/1999 | Konwitz | |
| 6,123,699 A | 9/2000 | Webster, Jr. | |
| 6,126,654 A | 10/2000 | Giba et al. | |
| 6,178,354 B1 | 1/2001 | Gibson | |
| 6,198,974 B1 | 3/2001 | Webster, Jr. | |
| 6,330,837 B1 | 12/2001 | Charles et al. | |
| 6,352,531 B1 | 3/2002 | O'Connor et al. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,533,772 B1 | 3/2003 | Sheds et al. | |
| 6,551,302 B1 | 4/2003 | Rosinko et al. | |
| 6,554,794 B1 | 4/2003 | Mueller et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,872,214 B2 | 3/2005 | Sonnenschein et al. | |
| 6,984,230 B2 | 1/2006 | Scheller et al. | |
| 7,004,957 B1 | 2/2006 | Dampney et al. | |
| 7,226,444 B1 | 6/2007 | Ellman et al. | |
| 7,303,533 B2 | 12/2007 | Johansen et al. | |
| 7,402,158 B2 | 7/2008 | Scheller et al. | |
| 7,555,327 B2 | 6/2009 | Matlock | |
| 7,632,242 B2 | 12/2009 | Griffin et al. | |
| 7,766,904 B2 | 10/2010 | McGowan, Sr. et al. | |
| 7,935,108 B2 | 5/2011 | Baxter et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,840,605 B2 | 9/2014 | Scheller et al. | |
| 8,840,607 B2 | 9/2014 | Scheller et al. | |
| 8,968,277 B2 | 1/2015 | Scheller et al. | |
| 8,951,245 B2 | 2/2015 | Scheller et al. | |
| 9,023,019 B2 | 5/2015 | Scheller et al. | |
| 9,023,020 B2 | 5/2015 | Scheller et al. | |
| 9,039,686 B2 | 5/2015 | Scheller et al. | |
| 9,089,399 B2 | 7/2015 | Scheller et al. | |
| 9,107,682 B2 | 8/2015 | Scheller et al. | |
| 9,113,995 B2 | 8/2015 | Scheller et al. | |
| 9,119,702 B2 | 9/2015 | Scheller et al. | |
| 9,138,346 B2 | 9/2015 | Scheller et al. | |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0131399 A1 | 6/2005 | Loeb et al. | |
| 2005/0154379 A1 | 7/2005 | McGowen, Sr. et al. | |
| 2005/0157985 A1 | 7/2005 | McGowan, Sr. et al. | |
| 2005/0234437 A1 | 10/2005 | Baxter et al. | |
| 2005/0272975 A1 | 12/2005 | McWeeny et al. | |
| 2005/0277874 A1 | 12/2005 | Selkee | |
| 2006/0129175 A1 | 6/2006 | Griffen et al. | |
| 2006/0178674 A1 | 8/2006 | McIntyre | |
| 2006/0293270 A1 | 12/2006 | Adamis et al. | |
| 2007/0179475 A1 | 8/2007 | Scheller | |
| 2007/0185514 A1 | 8/2007 | Kirchhevel | |
| 2007/0260231 A1 | 11/2007 | Rose et al. | |
| 2008/0132761 A1 | 6/2008 | Sonnenschein et al. | |
| 2008/0208105 A1 | 8/2008 | Zelickson et al. | |
| 2008/0287938 A1 | 11/2008 | Scheller et al. | |
| 2009/0018993 A1 | 1/2009 | Dick et al. | |
| 2009/0163943 A1 | 6/2009 | Cavanaugh et al. | |
| 2009/0187170 A1 | 7/2009 | Auld et al. | |
| 2009/0312750 A1 | 12/2009 | Spaide | |
| 2010/0004642 A1 | 1/2010 | Lumpkin | |
| 2010/0191224 A1 | 7/2010 | Butcher | |
| 2010/0208238 A1* | 8/2010 | Wilcken | G01J 3/02 356/51 |
| 2010/0268234 A1 | 10/2010 | Aho et al. | |
| 2010/0331883 A1 | 12/2010 | Schmitz et al. | |
| 2011/0028947 A1 | 2/2011 | Scheller et al. | |
| 2011/0144627 A1 | 6/2011 | Smith | |
| 2011/0144630 A1 | 6/2011 | Loeb | |
| 2011/0190749 A1 | 8/2011 | McMillian et al. | |
| 2011/0280653 A1 | 11/2011 | Sjostedt | |
| 2012/0116361 A1 | 5/2012 | Hanlon et al. | |
| 2012/0245569 A1 | 9/2012 | Papac et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0090635 A1 | 4/2013 | Mansour | |
| 2013/0096541 A1 | 4/2013 | Scheller et al. | |
| 2013/0116671 A1 | 5/2013 | Scheller et al. | |
| 2013/0144278 A1 | 6/2013 | Papac et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |
| 2013/0281994 A1 | 10/2013 | Scheller et al. | |
| 2013/0304043 A1 | 11/2013 | Scheller et al. | |
| 2013/0304048 A1 | 11/2013 | Scheller et al. | |
| 2014/0005642 A1 | 1/2014 | Scheller et al. | |
| 2014/0039471 A1 | 2/2014 | Scheller et al. | |
| 2014/0039472 A1 | 2/2014 | Scheller et al. | |
| 2014/0039475 A1 | 2/2014 | Scheller et al. | |
| 2014/0046307 A1 | 2/2014 | Scheller et al. | |
| 2014/0052115 A1 | 2/2014 | Zeid et al. | |
| 2014/0066907 A1 | 3/2014 | Scheller et al. | |
| 2014/0066912 A1 | 3/2014 | Scheller et al. | |
| 2014/0074073 A1 | 3/2014 | Scheller et al. | |
| 2014/0074079 A1 | 3/2014 | Scheller et al. | |
| 2014/0088572 A1 | 3/2014 | Scheller et al. | |
| 2014/0088576 A1 | 3/2014 | Scheller et al. | |
| 2014/0107628 A1 | 4/2014 | Scheller et al. | |
| 2014/0107629 A1 | 4/2014 | Scheller et al. | |
| 2015/0038950 A1 | 2/2015 | Scheller et al. | |

(56) References Cited

U.S. PATENT DOCUMENTS

2016/0100979 A1     4/2016   Scheller et al.
2016/0302878 A1    10/2016   Kern
2017/0135859 A1     5/2017   Scheller et al.

FOREIGN PATENT DOCUMENTS

WO    WO 2011/019581 A1    2/2001
WO    WO 2006/091597 A1    8/2006
WO    WO 2007/038433 A2    4/2007
WO    WO 2013/133717       9/2013

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

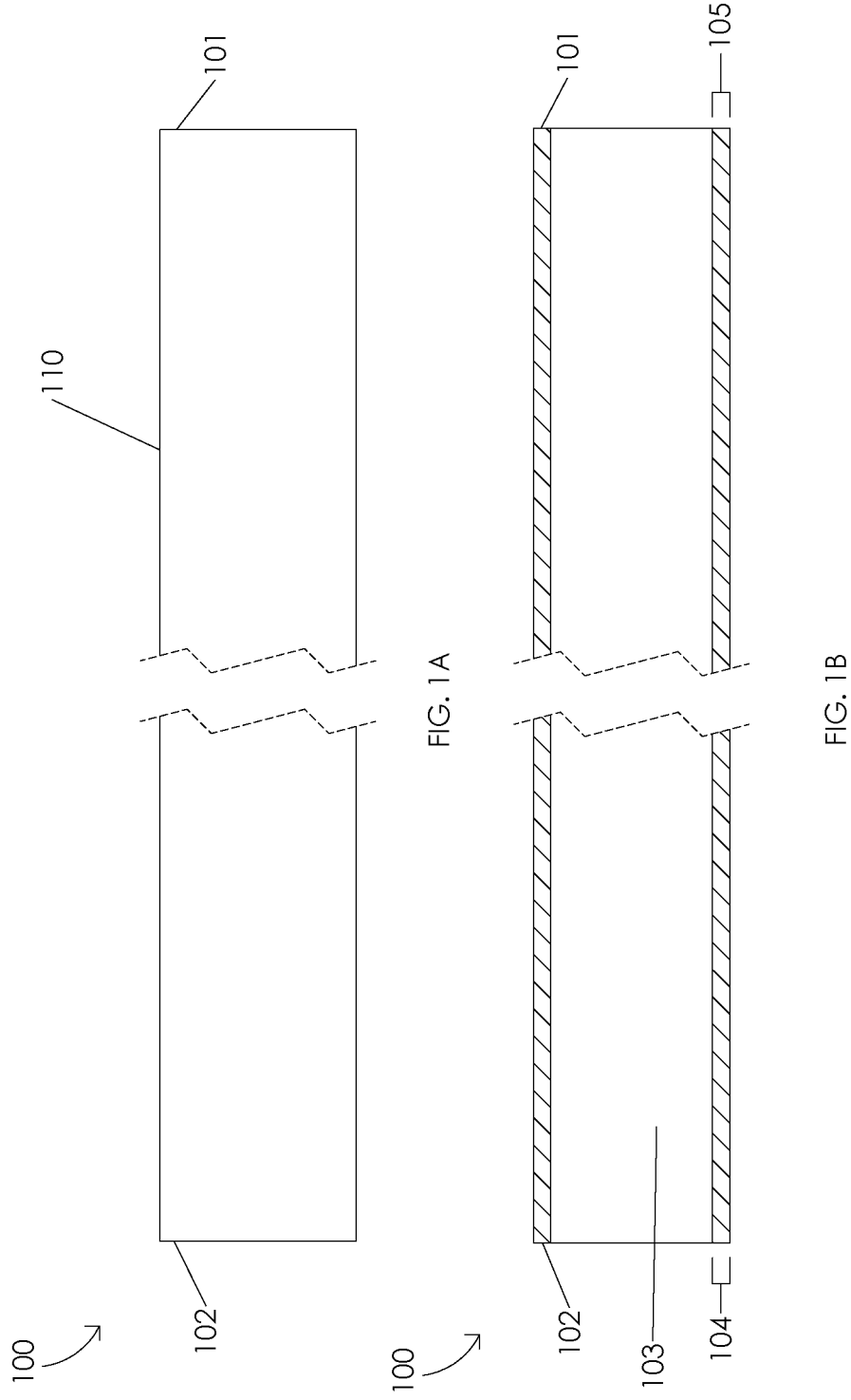

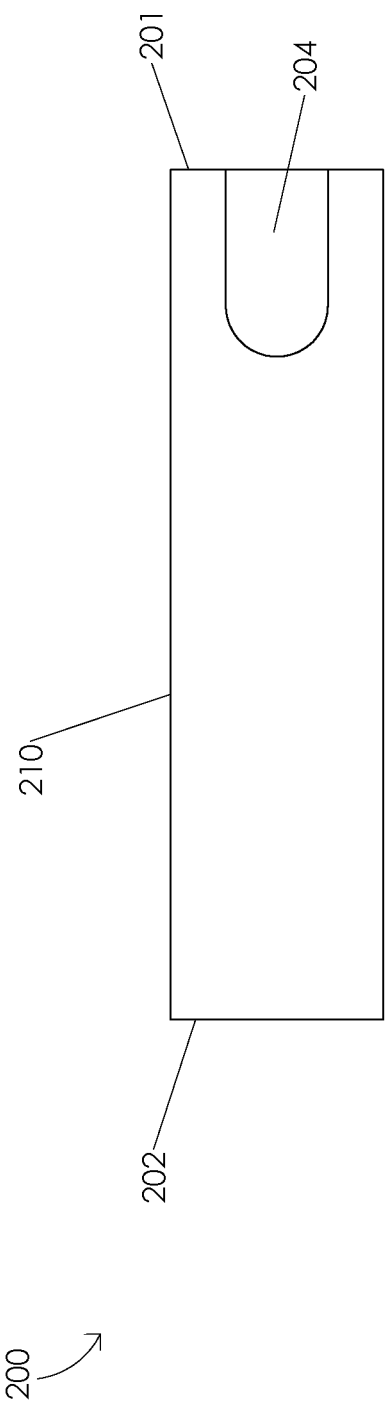
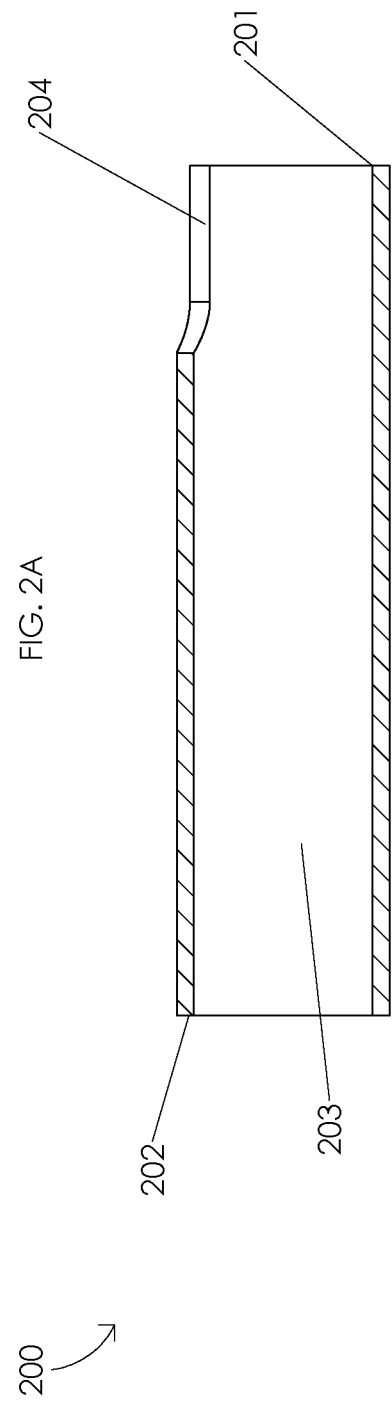

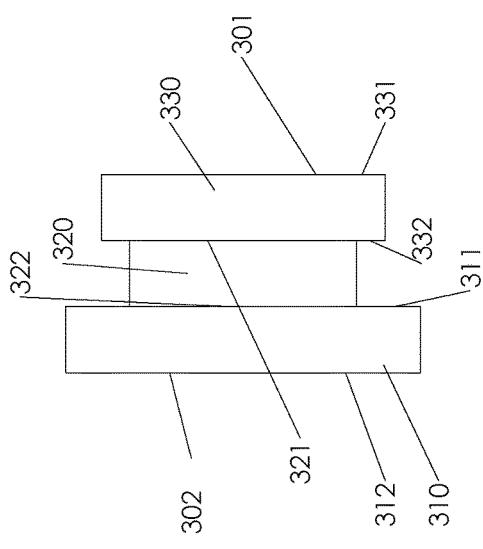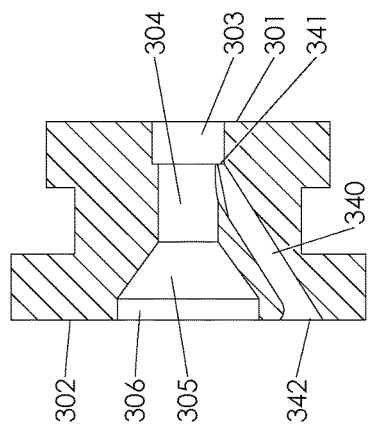

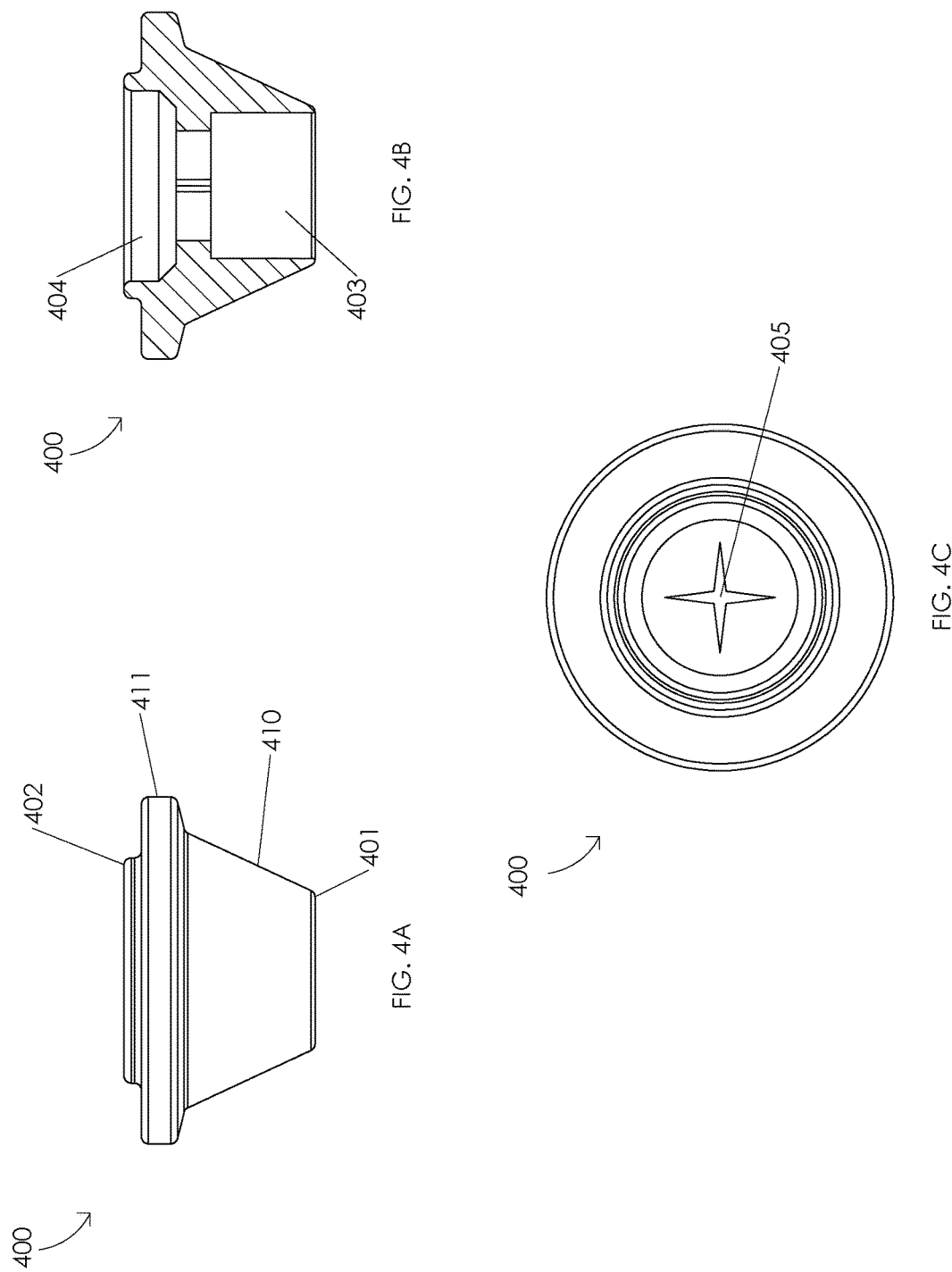

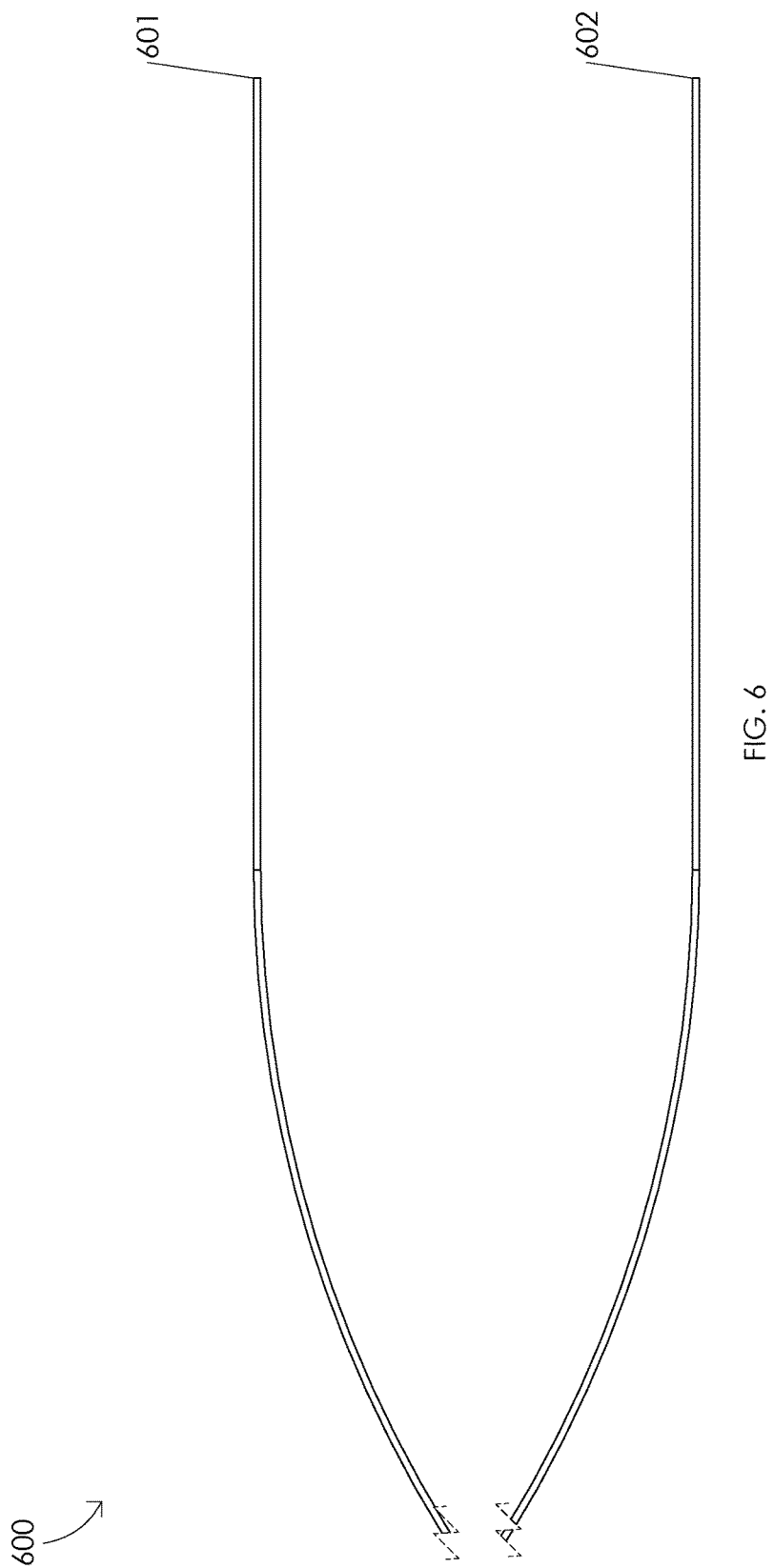

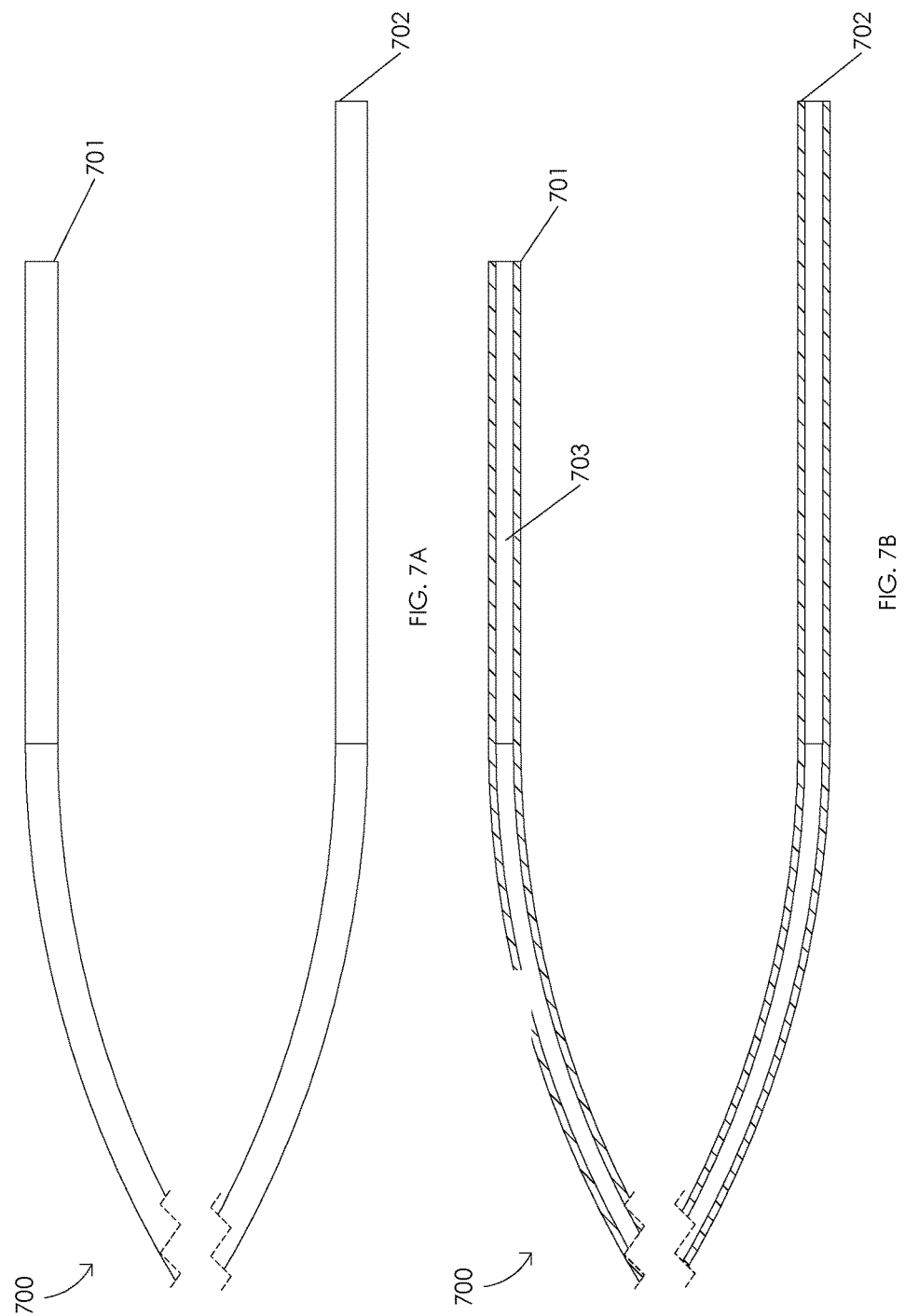

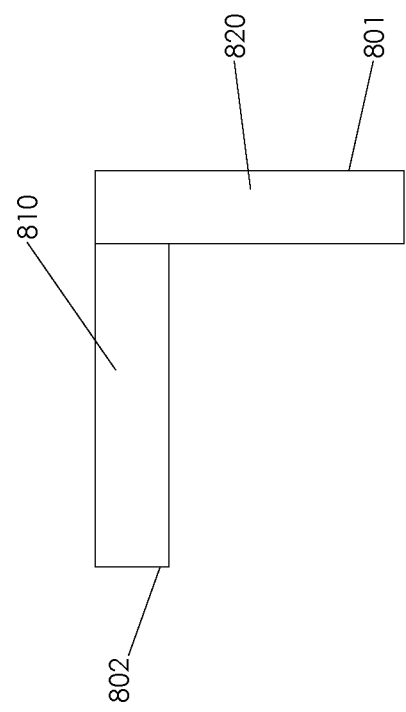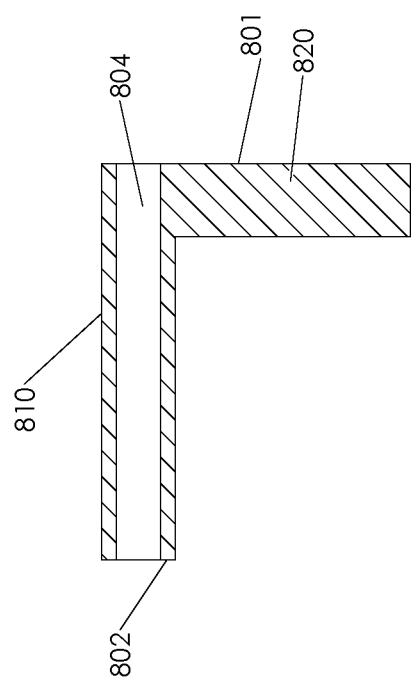

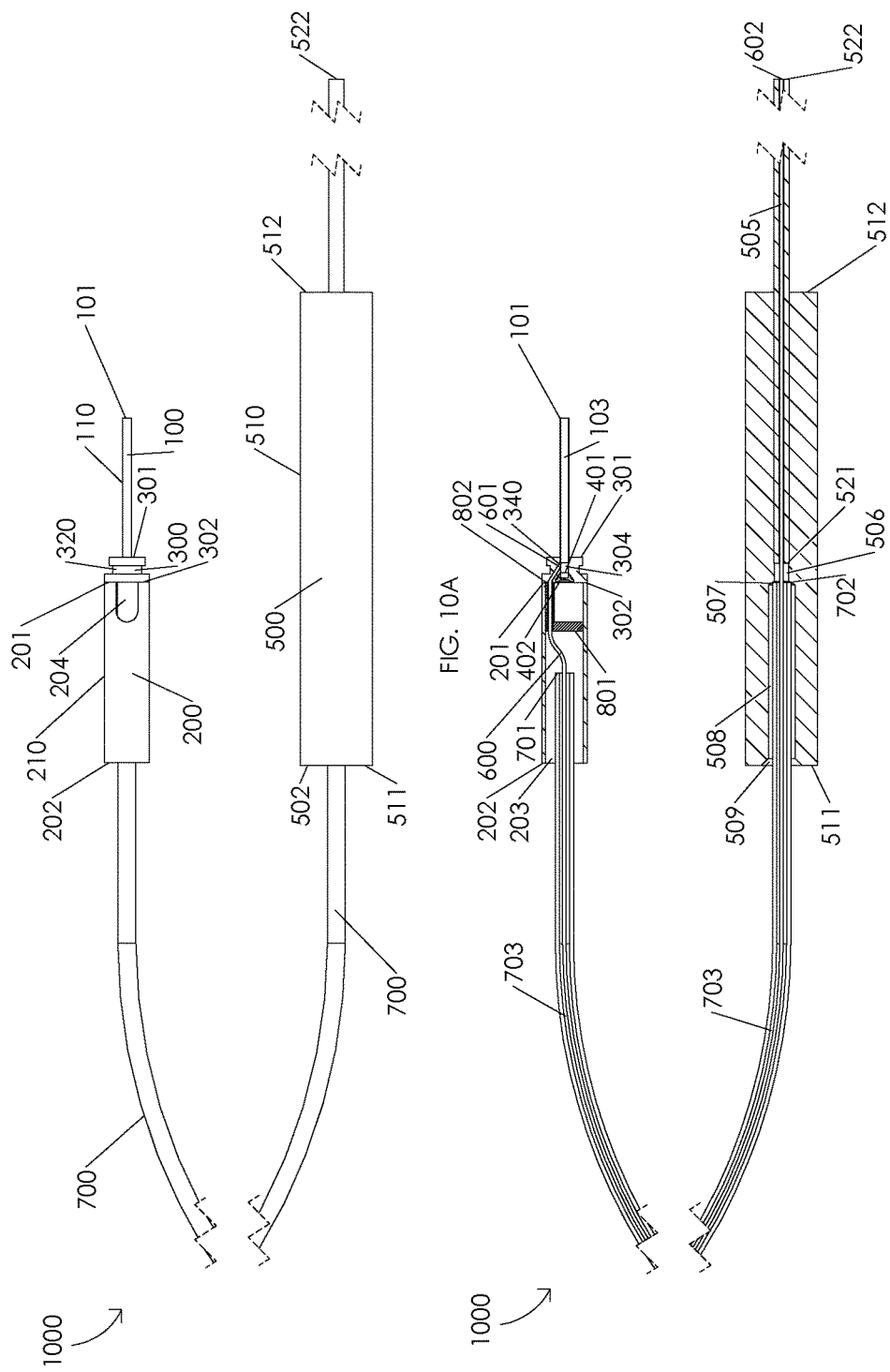

ILLUMINATED CANNULA

CROSS-REFERENCE TO RELATED APPLICATIONS

This application claims the benefit of U.S. Provisional Application No. 62/385,741, filed Sep. 9, 2016.

FIELD OF THE INVENTION

The present disclosure relates to a cannula, and, more particularly, to an illuminated cannula.

BACKGROUND OF THE INVENTION

Minimally invasive ophthalmic surgical procedures are typically performed through a cannula after making an incision in an eye. Use of the cannula in the incision may help reduce trauma to tissue and may also help maintain an intraocular pressure during a surgical procedure. For example, a surgeon may insert a forceps through a cannula to grasp and manipulate tissues during a surgical procedure.

BRIEF SUMMARY OF THE INVENTION

The present disclosure provides an illuminated cannula. Illustratively, an illuminated cannula may comprise an illumination tube, a hub, a cannula base, a valve, an illumination source connector, an optic fiber, and an optic fiber guide. In one or more embodiments, the valve may be disposed in the cannula base. Illustratively, the cannula base may be fixed to the hub. In one or more embodiments, the hub may comprise a hub aperture. Illustratively, the illumination tube may be disposed in the cannula base. In one or more embodiments, the optic fiber guide may be disposed in the hub. Illustratively, the optic fiber may be disposed in the illumination source connector, the hub, the optic fiber guide, and the cannula base. In one or more embodiments, the optic fiber may be optically coupled to the illumination tube. Illustratively, illumination light from an illumination source may be configured to transmit through the optic fiber and into the illumination tube.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating an illumination tube;

FIGS. 2A and 2B are schematic diagrams illustrating a hub;

FIGS. 3A and 3B are schematic diagrams illustrating a cannula base;

FIGS. 4A, 4B, and 4C are schematic diagrams illustrating a valve;

FIG. 6 is a schematic diagram illustrating an optic fiber;

FIGS. 7A and 7B are schematic diagrams illustrating a jacketing;

FIGS. 8A and 8B are schematic diagrams illustrating an optic fiber guide;

FIGS. 10A and 10B are schematic diagrams illustrating an assembled illuminated cannula;

DETAILED DESCRIPTION OF AN ILLUSTRATIVE EMBODIMENT

Figure 5A:
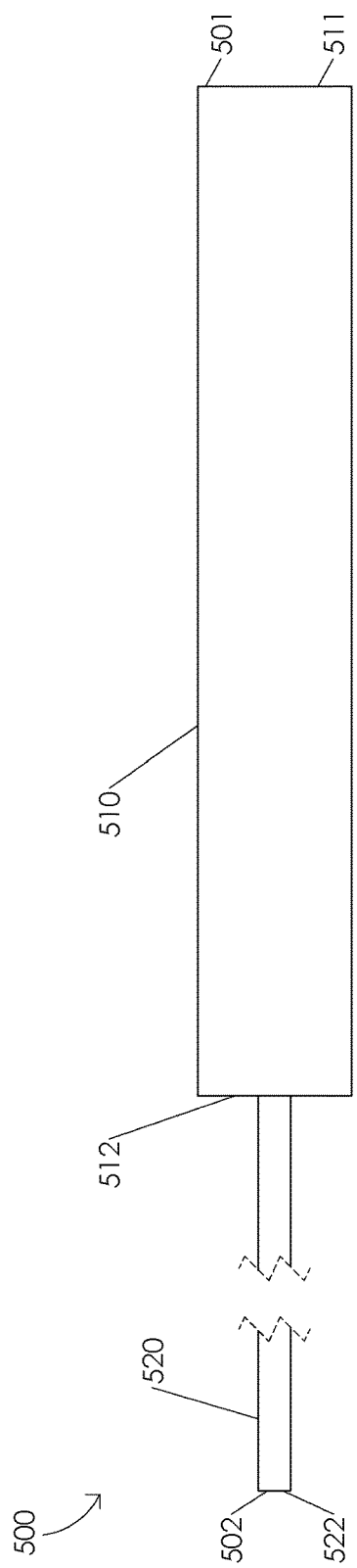
FIGS. 5A and 5B are schematic diagrams illustrating an illumination source connector.

FIGS. 1A and 1B are schematic diagrams illustrating an illumination tube 100. FIG. 1A illustrates a side view of an illumination tube 100. FIG. 1B illustrates a cross-sectional view in a sagittal plane of an illumination tube 100. Illustratively, illumination tube 100 may comprise an illumination tube distal end 101 and an illumination tube proximal end 102. In one or more embodiments, illumination tube 100 may comprise an inner bore 103. Illustratively, illumination tube 100 may comprise an incident width 104 and a transmission width 105. In one or more embodiments, illumination tube 100 may comprise an illumination tube outer surface 110. Illustratively, illumination tube 100 may be configured to transmit light, e.g., illumination tube 100 may be configured to transmit light to illuminate a surgical site. In one or more embodiments, illumination tube 100 may be manufactured from any suitable material, e.g., polymers, metals, metal alloys, etc., or from any combination of suitable materials. Illustratively, illumination tube 100 may be manufactured from silica. In one or more embodiments, illumination tube 100 may be manufactured from fluorine doped silica. Illustratively, illumination tube 100 may be manufactured from fused silica. In one or more embodiments, illumination tube 100 may be manufactured from poly(methyl methacrylate), an acrylate polymer, etc.

FIGS. 2A and 2B are schematic diagrams illustrating a hub 200. FIG. 2A illustrates a top view of a hub 200. FIG. 2B illustrates a cross-sectional view in a sagittal plane of a hub 200. Illustratively, hub 200 may comprise a hub distal end 201 and a hub proximal end 202. In one or more embodiments, hub 200 may comprise a hub inner lumen 203. Illustratively, hub 200 may comprise a hub aperture 204. In one or more embodiments, hub 200 may be manufactured from any suitable material, e.g., polymers, metals, metal alloys, etc., or from any combination of suitable materials.

FIGS. 3A and 3B are schematic diagrams illustrating a cannula base 300. FIG. 3A illustrates a side view of a cannula base 300. FIG. 3B illustrates a cross-sectional view in a sagittal plane of a cannula base 300. Illustratively, cannula base 300 may comprise a cannula base distal end 301 and a cannula base proximal end 302. In one or more embodiments, cannula base 300 may comprise an illumination tube housing 303, a cannula base inner lumen 304, a valve housing 305, and a flange interface 306. Illustratively, cannula base 300 may comprise an anterior lip 310. In one or more embodiments, anterior lip 310 may comprise an anterior lip distal end 311 and an anterior lip proximal end 312. Illustratively, cannula base 300 may comprise a posterior lip 330. In one or more embodiments, posterior lip 330 may comprise a posterior lip distal end 331 and a posterior lip proximal end 332. Illustratively, cannula base 300 may comprise a sclera interface 320, e.g., cannula base 300 may comprise a sclera interface 320 disposed between anterior lip 310 and posterior lip 330. In one or more embodiments, sclera interface 320 may comprise a sclera interface distal end 321 and a sclera interface proximal end 322. Illustratively, cannula base 300 may comprise an optic fiber lumen 340. In one or more embodiments, optic fiber lumen 340 may comprise an optic fiber lumen distal end 341 and an optic fiber lumen proximal end 342. Illustratively, optic fiber lumen 340 may be oriented at an angle relative to anterior lip proximal end 312, e.g., optic fiber lumen 340 may be oriented at an angle in a range of 40.0 to 75.0 degrees relative to anterior lip proximal end 312. In one or more embodiments, optic fiber lumen 340 may be oriented at an angle of 60.0 degrees relative to anterior lip proximal end 312. Illustratively, optic fiber lumen 340 may be oriented at an angle of less than 40.0 degrees or greater than 75.0 degrees relative to anterior lip proximal end 312. In one or more embodiments, optic fiber lumen 340 may taper into optic fiber lumen distal end 341, e.g., optic fiber lumen 340 may be configured to guide an optic fiber 600 into optic fiber lumen distal end 341. Illustratively, a portion of cannula base 300 may be configured to prevent an ingress of an optic fiber 600 into cannula base inner lumen 304, e.g., optic fiber lumen 340 and cannula base inner lumen 304 may be physically separated by a portion of cannula base 300. Illustratively, cannula base 300 may be manufactured from any suitable material, e.g., polymers, metals, metal alloys, etc., or from any combination of suitable materials.

In one or more embodiments, cannula base 300 may be manufactured from a material configured to deform if cannula base 300 is sterilized in a medical autoclave, e.g., cannula base 300 may be manufactured from a material configured to permanently deform if cannula base 300 is sterilized in a medical autoclave. Illustratively, cannula base 300 may be manufactured from a material having a melting point below a temperature parameter for a steam sterilization cycle, e.g., cannula base 300 may be manufactured from a material having a melting point below a temperature parameter for a gravity-displacement steam sterilization cycle, a dynamic-air-removal steam sterilization cycle, etc. In one or more embodiments, cannula base 300 may be manufactured from a material having a melting point below 140.0 degrees Fahrenheit. Illustratively, cannula base 300 may be manufactured from a material having a melting point in a range of 158.0 to 212.0 degrees Fahrenheit, e.g., cannula base 300 may be manufactured from a material having a melting point of 160.0 degrees Fahrenheit. In one or more embodiments, cannula base 300 may be manufactured from a material having a melting point of less than 158.0 degrees Fahrenheit or greater than 212.0 degrees Fahrenheit. In one or more embodiments, cannula base 300 may be manufactured from a material having a melting point below 250.0 degrees Fahrenheit. Illustratively, cannula base 300 may be manufactured from a material having a melting point below 270.0 degrees Fahrenheit. In one or more embodiments, cannula base 300 may be manufactured from a material having a melting point below 275.0 degrees Fahrenheit.

Illustratively, cannula base 300 may be manufactured from a material configured to temporarily deform if cannula base 300 is sterilized in a medical autoclave, e.g., cannula base 300 may be manufactured from a material configured to absorb water in a medical autoclave. In one or more embodiments, an absorption of water may be configured to deform cannula base 300, e.g., an absorption of water may be configured to cause cannula base 300 to expand. Illustratively, cannula base 300 may be manufactured from a porous material configured to facilitate a deformation of cannula base 300 if cannula base 300 is sterilized in a medical autoclave. In one or more embodiments, cannula base 300 may be manufactured with one or more cavities configured to facilitate a deformation of cannula base 300 if cannula base 300 is sterilized in a medical autoclave. Illustratively, cannula base 300 may be manufactured from any suitable material, e.g., polymers, metals, metal alloys, etc., or from any combination of suitable materials. In one or more embodiments, cannula base 300 may be manufactured by a 3D printing process. For example, cannula base 300 may be manufactured by selective laser sintering, selective heat sintering, selective laser melting, electron-beam melting, direct metal laser sintering, electron beam freeform fabrication, etc. Illustratively, cannula base 300 may be manufactured by injection molding. In one or more embodiments, cannula base 300 may be manufactured by additive manufacturing.

In one or more embodiments, cannula base 300 may be manufactured from poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly (hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc. Illustratively, cannula base 300 may be manufactured from any substituted polymers of poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4+alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)dipropionic anhydride], poly(ethelene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc.

FIGS. 4A, 4B, and 4C are schematic diagrams illustrating a valve 400. FIG. 4A illustrates a side view of a valve 400. FIG. 4B illustrates a cross-sectional view in a sagittal plane of a valve 400. FIG. 4C illustrates a top view of a valve 400. Illustratively, valve 400 may comprise a valve distal end 401 and a valve proximal end 402. In one or more embodiments, valve 400 may comprise a valve distal chamber 403 and a valve proximal chamber 404. Illustratively, valve 400 may comprise a valve port 405. In one or more embodiments, valve 400 may be configured to maintain an intraocular pressure, e.g., valve 400 may be configured to maintain an intraocular pressure during a surgical procedure. Illustratively, valve 400 may be manufactured from any suitable material, e.g., polymers, metals, metal alloys, etc., or from any combination of suitable materials.

Figure 5B:
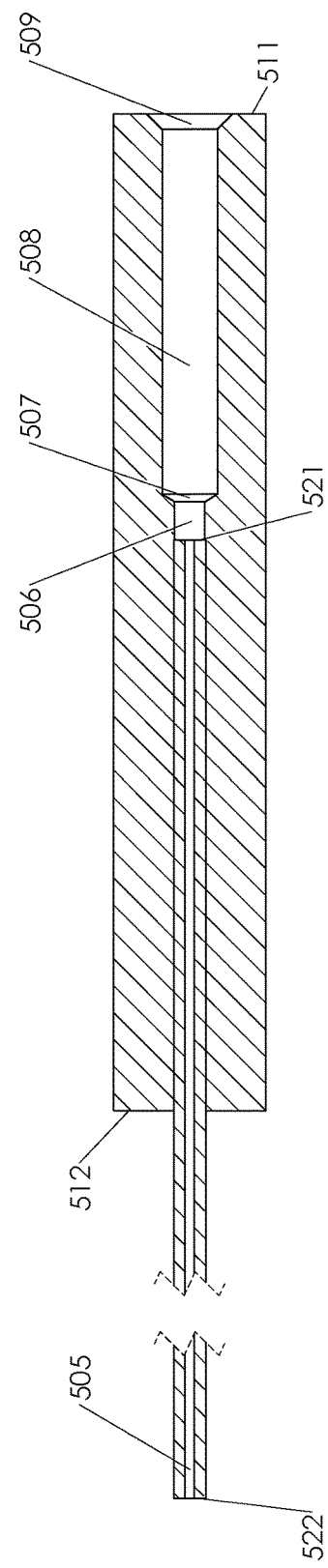

FIGS. 5A and 5B are schematic diagrams illustrating an illumination source connector 500. FIG. 5A illustrates a side view of an illumination source connector 500. FIG. 5B illustrates a cross-sectional view in a sagittal plane of an illumination source connector 500. Illustratively, illumination source connector 500 may comprise an illumination source connector distal end 501 and an illumination source connector proximal end 502. In one or more embodiments, illumination source connector 500 may comprise a connector base 510 and an optic fiber housing 520. Illustratively, connector base 510 may comprise a connector base distal end 511 and a connector base proximal end 512. In one or more embodiments, connector base 510 may comprise a connector base proximal inner bore 506, a connector base proximal taper 507, a connector base distal inner bore 508, and a connector base distal taper 509. Illustratively, optic fiber housing 520 may comprise an optic fiber housing distal end 521 and an optic fiber housing proximal end 522. In one or more embodiments, optic fiber housing 520 may comprise an optic fiber housing inner bore 505. Illustratively, a portion of optic fiber housing 520 may be disposed in a portion of connector base 510, e.g., optic fiber housing distal end 521 may be disposed in connector base proximal inner bore 506. In one or more embodiments, a portion of optic fiber housing 520 may be disposed in a portion of connector base 510 wherein optic fiber housing proximal end 522 extends a distance out from connector base proximal end 512. Illustratively, a portion of optic fiber housing 520 may be fixed in a portion of connector base 510, e.g., a portion of optic fiber housing 520 may be fixed in a portion of connector base 510 by an interference fit, an adhesive, an epoxy, a setscrew, a tie, a magnetic field, a weld, a threading, etc. In one or more embodiments, connector base 500 may be manufactured from any suitable material, e.g., polymers, metals, metal alloys, etc., or from any combination of suitable materials.

FIG. 6 is a schematic diagram illustrating an optic fiber 600. In one or more embodiments, optic fiber 600 may comprise an optic fiber distal end 601 and an optic fiber proximal end 602. Illustratively, optic fiber 600 may be configured to transmit light from a surgical illumination source, e.g., light from a surgical illumination source may ingress optic fiber 600 at optic fiber proximal end 602 and light from a surgical illumination source may egress optic fiber 600 at optic fiber distal end 601. In one or more embodiments, optic fiber 600 may comprise a single optic fiber. Illustratively, optic fiber 600 may comprise a plurality of optic fibers. In one or more embodiments, optic fiber 600 may comprise one or more optic fibers manufactured from silica. Illustratively, optic fiber 600 may comprise one or more optic fibers manufactured from plastic, e.g., optic fiber 600 may comprise one or more optic fibers manufactured from Polymethyl Methacrylate Resin, Polystyrene, etc. In one or more embodiments, optic fiber 600 may comprise one or more optic fibers having a cladding material, e.g., optic fiber 600 may comprise one or more optic fibers having a cladding material manufactured from a fluorinated polymer, a silicone resin, etc. Illustratively, optic fiber 600 may comprise one or more optic fibers having a step index refractive index profile. In one or more embodiments, optic fiber 600 may comprise one or more multi-mode optic fibers, one or more single-mode optic fibers, etc. In one or more embodiments, optic fiber 600 may comprise one or more optic fibers having a core refractive index in a range of 1.3 to 1.8, e.g., optic fiber 600 may comprise one or more optic fibers having a core refractive index of 1.49. Illustratively, optic fiber 600 may comprise one or more optic fibers having a core refractive index of less than 1.3 or greater than 1.8. In one or more embodiments, optic fiber 600 may comprise one or more optic fibers having a numerical aperture in a range of 0.3 to 0.8, e.g., optic fiber 600 may comprise one or more optic fibers having a numerical aperture of 0.5. In one or more embodiments, optic fiber 600 may comprise one or more optic fibers having a numerical aperture of less than 0.3 or greater than 0.8. Illustratively, optic fiber 600 may be configured to transmit light from an illumination source having a focal spot diameter in a range of 20.0 to 60.0 micrometers, e.g., optic fiber 600 may be configured to transmit light from an illumination source having a focal spot diameter of 40.0 micrometers. In one or more embodiments, optic fiber 600 may be configured to transmit light from an illumination source having a focal spot diameter of less than 20.0 micrometers or greater than 60.0 micrometers. Illustratively, optic fiber 600 may have an outer diameter in a range of 50.0 to 750.0 micrometers, e.g., optic fiber 600 may have an outer diameter of 100.0 micrometers. In one or more embodiments, optic fiber 600 may have an outer diameter of less than 50.0 micrometers or greater than 750.0 micrometers.

FIGS. 7A and 7B are schematic diagrams illustrating a jacketing 700. FIG. 7A illustrates a side view of a jacketing 700. FIG. 7B illustrates a cross-sectional view in a sagittal plane of a jacketing 700. Illustratively, jacketing 700 may comprise a jacketing distal end 701 and a jacketing proximal end 702. In one or more embodiments, jacketing 700 may comprise a jacketing inner diameter 703. Illustratively, jacketing 700 may be manufactured from any suitable material, e.g., polymers, metals, metal alloys, etc., or from any combination of suitable materials.

FIGS. 8A and 8B are schematic diagrams illustrating an optic fiber guide 800. FIG. 8A illustrates a side view of an optic fiber guide 800. FIG. 8B illustrates a cross-sectional view in a sagittal plane of an optic fiber guide 800. Illustratively, optic fiber guide 800 may comprise an optic fiber guide distal end 801 and an optic fiber guide proximal end 802. In one or more embodiments, optic fiber guide 800 may comprise an optic fiber guide inner lumen 804. Illustratively, optic fiber guide 800 may comprise an optic fiber shield 810 and an optic fiber guide base 820. In one or more embodiments, optic fiber shield 810 may be configured to protect a portion of optic fiber 600, e.g., optic fiber shield 810 may be configured to prevent a portion of optic fiber 600 from being damaged. Illustratively, optic fiber guide may be manufactured from any suitable material, e.g., polymers, metals, metal alloys, etc., or from any combination of suitable materials.

Figure 9:
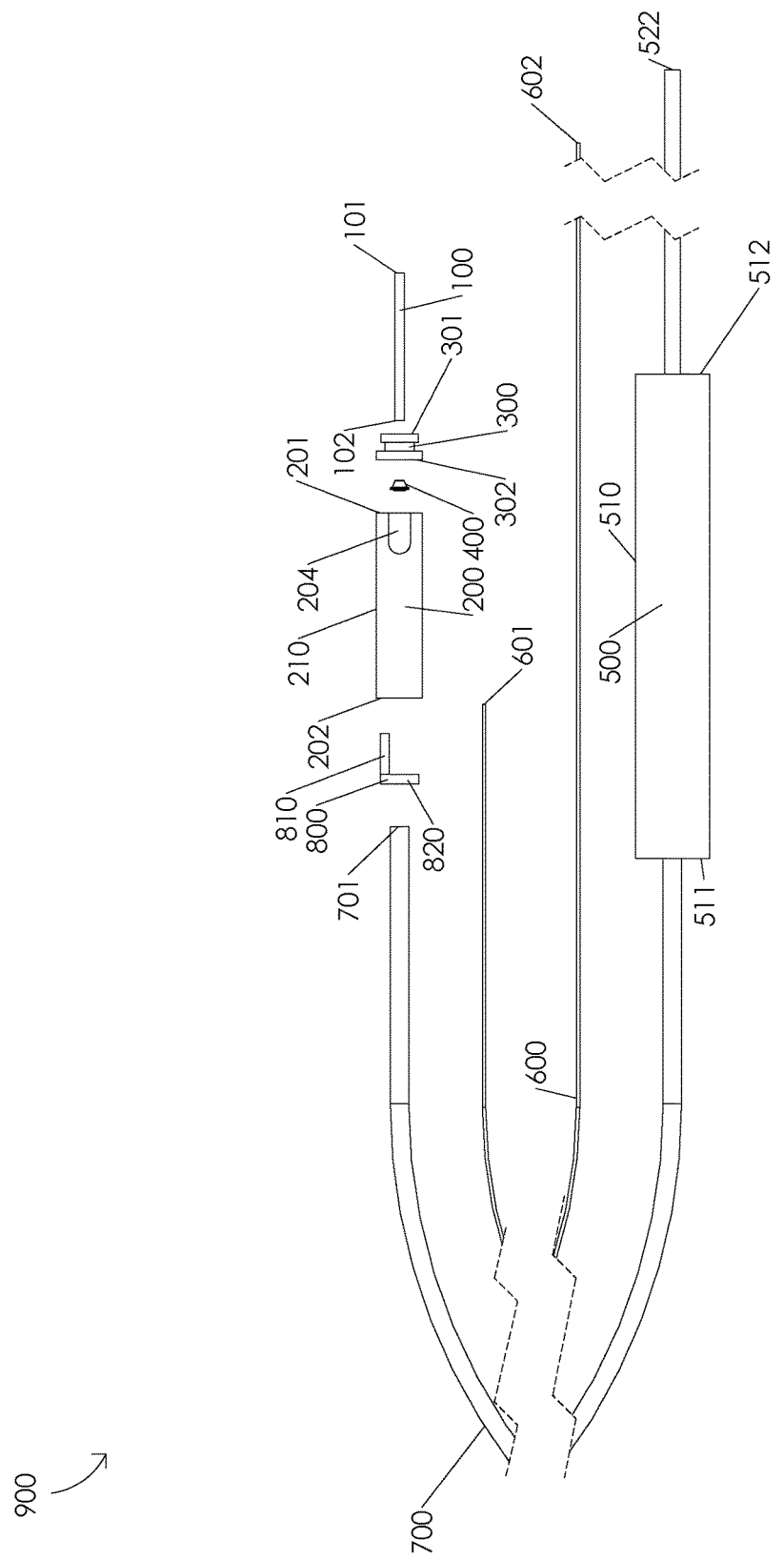
FIG. 9 is a schematic diagram illustrating an exploded view of an illuminated cannula assembly.

FIG. 9 is a schematic diagram illustrating an exploded view of an illuminated cannula assembly 900. Illustratively, an illuminated cannula assembly 900 may comprise an illumination tube 100, a hub 200, a cannula base 300, a valve 400, an illumination source connector 500, an optic fiber 600, a jacketing 700, and an optic fiber guide 800.

FIGS. 10A and 10B are schematic diagrams illustrating an assembled illuminated cannula 1000. FIG. 10A illustrates a side view of an assembled illuminated cannula 1000. FIG. 10B illustrates a cross-sectional view in a sagittal plane of an assembled illuminated cannula 1000. In one or more embodiments, a portion of optic fiber 600 may be disposed in jacketing 700, e.g., a portion of optic fiber 600 may be disposed in jacketing inner diameter 703. Illustratively, optic fiber 600 may be disposed in jacketing 700 wherein optic fiber distal end 601 extends out from jacketing distal end 701. In one or more embodiments, optic fiber 600 may be disposed in jacketing 700 wherein optic fiber proximal end 602 extends out from jacketing proximal end 702. Illustratively, a portion of optic fiber 600 may be fixed in a portion of jacketing 700, e.g., a portion of optic fiber 600 may be fixed in a portion of jacketing 700 by an interference fit, an adhesive, an epoxy, a setscrew, a crimp, etc. In one or more embodiments, a portion of jacketing 700 may be disposed in a portion of illumination source connector 500, e.g., jacketing proximal end 702 may be disposed in connector base distal inner bore 508. Illustratively, a portion of jacketing 700 may be fixed in a portion of illumination source connector 500, e.g., a portion of jacketing 700 may be fixed in a portion of illumination source connector 500 by an interference fit, an adhesive, an epoxy, a setscrew, a tie, a crimp, a weld, etc. In one or more embodiments, a portion of optic fiber 600 may be disposed in illumination source connector 500, e.g., optic fiber proximal end 602 may be disposed in illumination source connector 500. Illustratively, optic fiber 600 may be disposed in connector base distal taper 509, connector base distal inner bore 508, connector base proximal taper 507, connector base proximal inner bore 506, and optic fiber housing inner bore 505. In one or more embodiments, optic fiber 600 may be disposed in illumination source connector 500 wherein optic fiber proximal end 602 is adjacent to illumination source connector proximal end 502, e.g., optic fiber 600 may be disposed in illumination source connector 500 wherein optic fiber proximal end 602 is adjacent to optic fiber housing proximal end 522. Illustratively, optic fiber 600 may be disposed in illumination source connector 500 wherein optic fiber proximal end 602 abuts illumination source connector proximal end 502, e.g., optic fiber 600 may be disposed in illumination source connector 500 wherein optic fiber proximal end 602 abuts optic fiber housing proximal end 522. In one or more embodiments, optic fiber 600 may be disposed in illumination source connector 500 wherein optic fiber proximal end 602 is coplanar with illumination source connector proximal end 502, e.g., optic fiber 600 may be disposed in illumination source connector 500 wherein optic fiber proximal end 602 is coplanar with optic fiber housing proximal end 522. Illustratively, a portion of optic fiber 600 may be fixed in a portion of illumination source connector 500, e.g., a portion of optic fiber 600 may be fixed in a portion of illumination source connector 500 by an interference fit, an adhesive, an epoxy, a setscrew, a crimp, etc.

In one or more embodiments, a portion of jacketing 700 may be disposed in a portion of hub 200, e.g., jacketing distal end 701 may be disposed in hub inner lumen 203. Illustratively, a portion of jacketing 700 may be fixed in a portion of hub 200, e.g., a portion of jacketing 700 may be fixed in a portion of hub 200 by an interference fit, an adhesive, an epoxy, a setscrew, a crimp, etc. In one or more embodiments, a portion of valve 400 may be disposed in a portion of cannula base 300, e.g., valve distal end 401 may be disposed in cannula base 300. Illustratively, a portion of valve 400 may be disposed in valve housing 305, e.g., a portion of valve 400 may be disposed in valve housing 305 wherein flange 411 is adjacent to flange interface 411. In one or more embodiments, a portion of valve 400 may be disposed in valve housing 305 wherein flange 411 abuts flange interface 411. Illustratively, a portion of valve 400 may be fixed in a portion of cannula base 300, e.g., a portion of valve 400 may be fixed in a portion of cannula base 300 by an interference fit, an adhesive, an epoxy, a setscrew, a tie, a crimp, a weld, a threading, a pin, etc.

In one or more embodiments, a portion of cannula base 300 may be fixed to a portion of hub 200, e.g., cannula base proximal end 302 may be fixed to hub distal end 201. Illustratively, a portion of cannula base 300 may be fixed in a portion of hub 200, e.g., a portion of cannula base 300 may be fixed in hub inner lumen 203. In one or more embodiments, hub distal end 201 may be adjacent to cannula base proximal end 302, e.g., hub distal end 201 may be adjacent to anterior lip proximal end 312. Illustratively, hub distal end 201 may abut cannula base proximal end 302, e.g., hub distal end 201 may abut anterior lip proximal end 312. In one or more embodiments, a portion of cannula base 300 may be fixed to a portion of hub 200 by an interference fit, an adhesive, an epoxy, a setscrew, a tie, a crimp, a weld, a threading, a pin, etc. Illustratively, an interface between cannula base proximal end 302 and hub distal end 201 may be configured to form a hermetic seal. In one or more embodiments, a portion of cannula base 300 may be disco posed in a portion of hub 200, e.g., cannula base proximal end 302 may be disposed in a portion of hub 200. Illustratively, a portion of cannula base 300 may be fixed in a portion of hub 200 by an interference fit, an adhesive, an epoxy, a setscrew, a tie, a crimp, a weld, a threading, a pin, a heat shrink, etc. In one or more embodiments, an interface between cannula base proximal end 302 and hub 200 may be configured to form a hermetic seal.

Illustratively, a portion of illumination tube 100 may be disposed in a portion of cannula base 300, e.g., illumination tube proximal end 102 may be disposed in illumination tube housing 303. In one or more embodiments, a portion of illumination tube 100 may be disposed in a portion of cannula base 300 wherein illumination tube proximal end 102 is adjacent to optic fiber lumen distal end 341, e.g., a portion of illumination tube 100 may be disposed in a portion of cannula base 300 wherein incident width 104 is adjacent to optic fiber lumen distal end 341. Illustratively, a portion of illumination tube 100 may be disposed in a portion of cannula base 300 wherein illumination tube proximal end 102 abuts optic fiber lumen distal end 341, e.g., a portion of illumination tube 100 may be disposed in a portion of cannula base 300 wherein incident width 104 abuts optic fiber lumen distal end 341. In one or more embodiments, a portion of illumination tube 100 may be disposed in a portion of cannula base 300 wherein illumination tube proximal end 102 is coplanar with optic fiber lumen distal end 341, e.g., a portion of illumination tube 100 may be disposed in a portion of cannula base 300 wherein incident width 104 is coplanar with optic fiber lumen proximal end 342. Illustratively, a portion of illumination tube 100 may be fixed in a portion of cannula base 300 by an interference fit, an adhesive, an epoxy, a setscrew, a tie, a crimp, a weld, a threading, a pin, a heat shrink, etc.

In one or more embodiments, optic fiber guide 800 may be disposed in a portion of hub 200, e.g., optic fiber guide 800 may be disposed in hub inner lumen 203. Illustratively, optic fiber guide 800 may be disposed in hub 200 wherein optic fiber shield 210 is disposed superior to hub aperture 204, e.g., optic fiber guide 800 may be disposed in hub inner lumen 203 wherein optic fiber shield 210 is superior to hub aperture 204. In one or more embodiments, optic fiber guide 800 may be disposed in hub 200 wherein optic fiber shield 200 is disposed inferior to hub aperture 204, e.g., optic fiber guide 800 may be disposed in hub inner lumen 203 wherein optic fiber shield 210 is inferior to hub aperture 204. Illustratively, optic fiber guide 800 may be disposed in hub 200 wherein optic fiber guide proximal end 802 is adjacent to cannula base proximal end 302. In one or more embodiments, optic fiber guide 800 may be disposed in hub 200 wherein optic fiber guide proximal end 802 abuts cannula base proximal end 302. Illustratively, optic fiber guide 800 may be disposed in hub 200 wherein optic fiber guide proximal end 802 is adjacent to anterior lip proximal end 312. In one or more embodiments, optic fiber guide 800 may be disposed in hub 200 wherein optic fiber guide proximal end 802 abuts anterior lip proximal end 312. Illustratively, optic fiber guide 800 may be disposed in hub 200 wherein optic fiber guide inner lumen 804 is collinear with optic fiber lumen proximal end 342. In one or more embodiments, a portion of optic fiber guide 800 may be fixed to a portion of cannula base 300 by an interference fit, an adhesive, an epoxy, a setscrew, a tie, a crimp, a weld, a threading, a pin, a heat shrink, etc. Illustratively, optic fiber guide 800 may be fixed in a portion of hub 200 by an interference fit, an adhesive, an epoxy, a setscrew, a tie, a crimp, a weld, a threading, a pin, a heat shrink, etc.

In one or more embodiments, a portion of optic fiber 600 may be disposed in a portion of hub 200, e.g., a portion of optic fiber 600 may be disposed in hub inner lumen 203. Illustratively, a portion of optic fiber 600 may be disposed in a portion of optic fiber guide 800, e.g., a portion of optic fiber 600 may be disposed in optic fiber shield 810. In one or more embodiments, optic fiber 600 may be disposed in optic fiber shield 810 wherein optic fiber distal end 601 extends out from optic fiber shield 810, e.g., optic fiber 600 may be disposed in optic fiber shield 810 wherein optic fiber distal end 601 extends out from optic fiber guide proximal end 802. In one or more embodiments, a portion of optic fiber 600 may be disposed in a portion of optic fiber guide 800 wherein optic fiber guide 800 is configured to maintain a disposition of the portion of optic fiber 600 superior to hub aperture 204. Illustratively, a portion of optic fiber 600 may be disposed in a portion of optic fiber guide 800 wherein optic fiber guide 800 is configured to maintain a disposition of the portion of optic fiber 600 inferior to hub aperture 204. In one or more embodiments, a portion of optic fiber 600 may be fixed in a portion of optic fiber guide 800 by an interference fit, an adhesive, an epoxy, a setscrew, a tie, a crimp, a weld, a threading, a pin, a heat shrink, etc.

Illustratively, a portion of optic fiber 600 may be disposed in cannula base 300, e.g., a portion of optic fiber 600 may be disposed in optic fiber lumen 340. In one or more embodiments, optic fiber 600 may ingress optic fiber lumen 340 at optic fiber lumen proximal end 342. Illustratively, optic fiber 600 may egress optic fiber lumen 340 at optic fiber lumen distal end 341. In one or more embodiments, optic fiber 600 may be disposed in optic fiber lumen 340 wherein a portion of optic fiber 600 extends out from optic fiber lumen distal end 341, e.g., optic fiber 600 may be disposed in optic fiber lumen 340 wherein optic fiber distal end 601 extends out from optic fiber lumen distal end 341. Illustratively, optic fiber distal end 601 may be disposed in cannula base inner lumen 304. In one or more embodiments, optic fiber distal end 601 may be prevented from an ingress into cannula base inner lumen 304, e.g., a portion of cannula base 300 may partition optic fiber lumen 340 and cannula base inner lumen 304. Illustratively, a portion of cannula base 300 may comprise a partition configured to separate optic fiber lumen 340 and cannula base inner lumen 304, e.g., a portion of cannula base 300 may comprise a partition configured to physically separate optic fiber lumen 340 and cannula base inner lumen 304. In one or more embodiments, optic fiber lumen 340 may comprise a tapered portion configured to guide optic fiber distal end 601 out from optic fiber lumen distal end 341, e.g., optic fiber lumen 340 may comprise a tapered portion configured to guide optic fiber distal end 601 out from optic fiber lumen distal end 341 wherein optic fiber distal end 601 is disposed flush with incident width 104. Illustratively, optic fiber lumen 340 may comprise a tapered portion configured to guide optic fiber distal end 601 out from optic fiber lumen distal end 341 wherein optic fiber distal end 601 is disposed flush with illumination tube proximal end 102. In one or more embodiments, optic fiber lumen 340 may comprise a tapered portion configured to optically couple optic fiber distal end 601 and incident width 104, e.g., optic fiber lumen 340 may comprise a tapered portion configured to optically couple optic fiber distal end 601 and illumination tube proximal end 102. Illustratively, optic fiber distal end 601 may be fixed to incident width 104, e.g., optic fiber distal end 601 may be fixed to illumination tube proximal end 102. In one or more embodiments, optic fiber distal end 601 may be thermally fused to incident width 104, e.g., optic fiber distal end 601 may be thermally fused to illumination tube proximal end 102. Illustratively, a portion of optic fiber 600 may be fixed to a portion of illumination tube 100 by an interference fit, an adhesive, an epoxy, a setscrew, a tie, a crimp, a weld, a threading, a pin, a heat shrink, etc. In one or more embodiments, a portion of optic fiber 600 may be fixed to a portion of illumination tube 100 by an epoxy configured to transmit light from an illumination source. Illustratively, a portion of optic fiber 600 may be fixed in optic fiber guide 800 by an interference fit, an adhesive, an epoxy, a setscrew, a tie, a crimp, a weld, a threading, a pin, a heat shrink, etc. In one or more embodiments, illumination tube 100 may comprise a bore for coupling illumination tube 100 and optic fiber 600, e.g., incident width 104 may comprise a bore configured to house optic fiber distal end 601. Illustratively, a portion of illumination tube 100 may comprise a lens configured to optically couple optic fiber distal end 601 and illumination tube proximal end 102, e.g., a portion of illumination tube 100 may comprise a convex-concave lens configured to optically couple optic fiber distal end 601 and illumination tube proximal end 102.

In one or more embodiments, illumination source connector 500 may be configured to connect to an illumination source. Illustratively, an illumination source may be configured to transmit illumination light into optic fiber proximal end 602, through optic fiber 600, out from optic fiber distal end 601, into incident width 104, through illumination tube 100, and out from transmission width 105, e.g., an illumination source may be configured to transmit illumination light into optic fiber proximal end 602, through optic fiber 600, out from optic fiber distal end 601, into illumination tube proximal end 102, through illumination tube 100, and out from illumination tube distal end 101 to illuminate a surgical site. In one or more embodiments, incident width 104 may be a first width and transmission width 105 may be a second width. Illustratively, the first width may be equal to the second width, e.g., illumination tube 100 may be configured to provide midfield illumination. In one or more embodiments, the first width may be larger than the second width, e.g., illumination tube 100 may be configured to provide nearfield illumination. Illustratively, the first width may be smaller than the second width, e.g., illumination tube 100 may be configured to provide widefield illumination. In one or more embodiments, illumination tube distal end 101 may be modified to adjust one or more properties of an illumination spot projected by transmission width 105. Illustratively, illumination tube distal end 101 may be tapered wherein transmission width 105 is gradually increased to increase an illumination spot size. In one or more embodiments, illumination tube distal end 101 may be tapered wherein transmission width 105 is gradually decreased to decrease an illumination spot size. Illustratively, illumination tube distal end 101 may be convex to decrease light divergence. In one or more embodiments, illumination tube distal end 101 may be concave to increase light divergence.

Figure 11A:
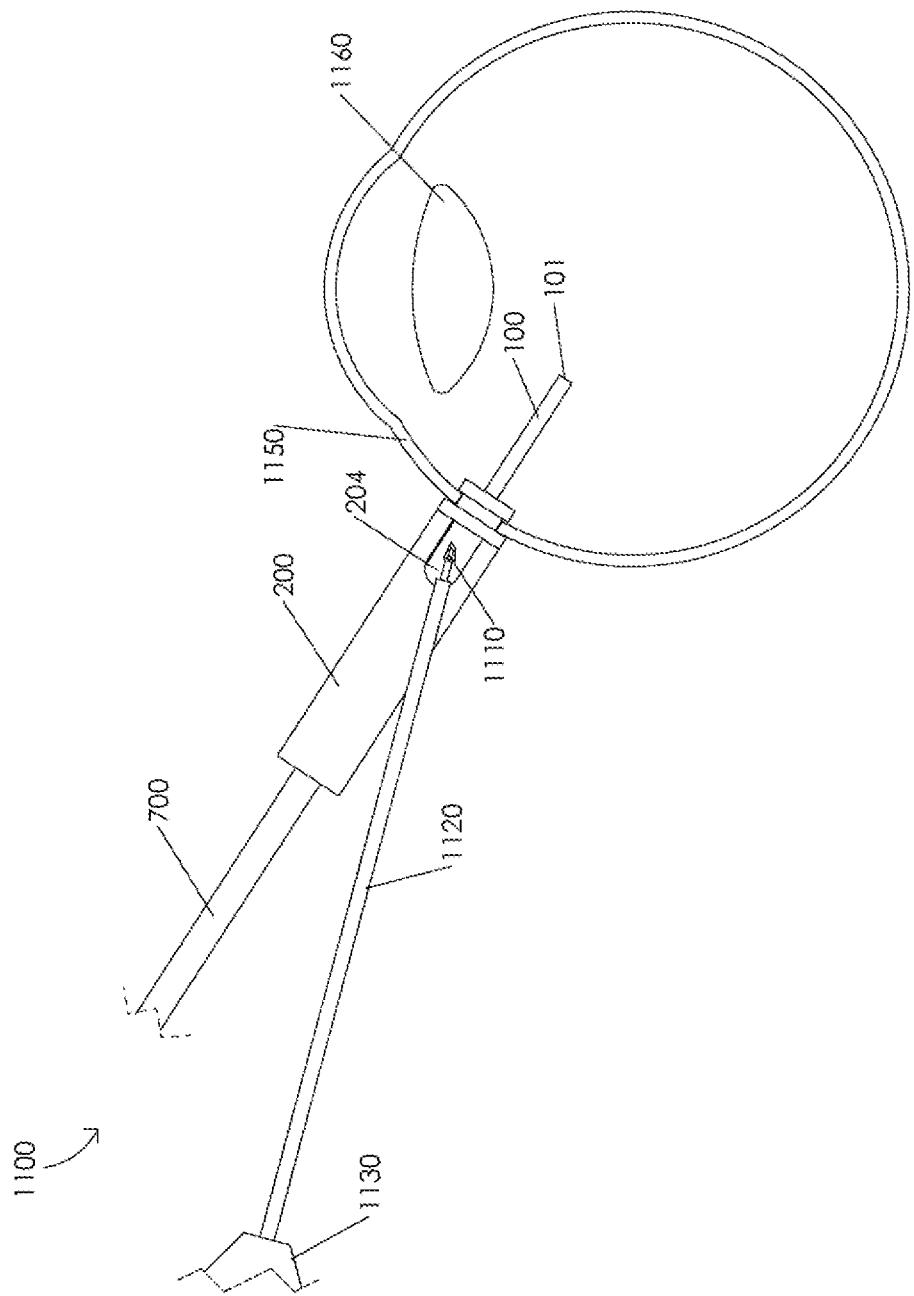
FIGS. 11A and 11B are schematic diagrams illustrating an instrument insertion in an illuminated cannula.
Figure 11B:
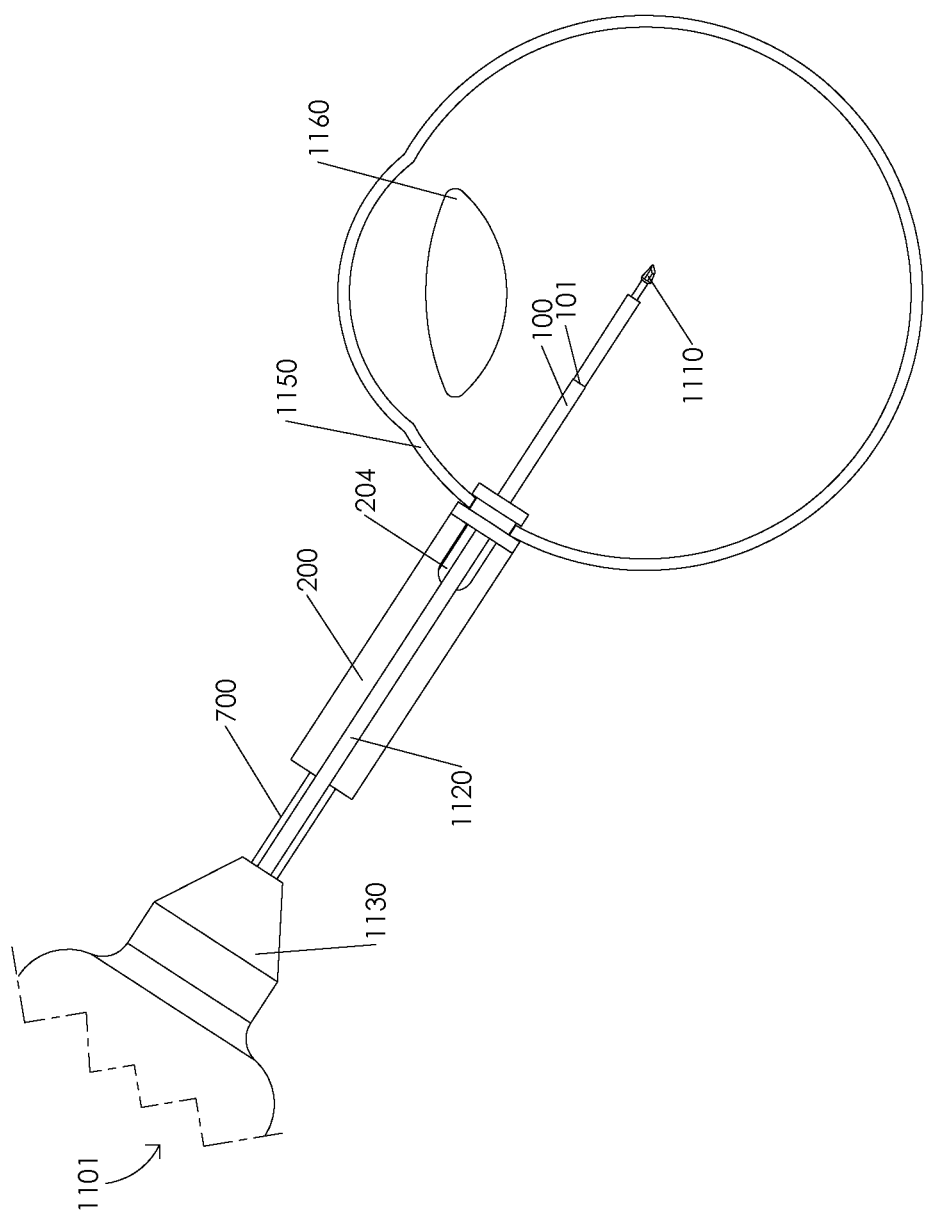

FIGS. 11A and 11B are schematic diagrams illustrating an instrument insertion in an illuminated cannula. Illustratively, an instrument may comprise an instrument tip 1110, a hypodermic tube 1120, and a handle 1130. FIG. 11A illustrates an initial insertion 1100. In one or more embodiments, a surgeon may insert cannula base 300 in an incision configured to avoid a contact with lens 1160. Illustratively, cannula base 300 may be disposed in an incision wherein anterior lip 310 is disposed superior to sclera 1150 and posterior lip 330 is disposed inferior to sclera 1150. In one or more embodiments, cannula base 300 may be disposed in an incision wherein sclera interface 320 is configured to interface with sclera 1150. Illustratively, a surgeon may perform an initial insertion 1100 by guiding instrument tip 1110 into hub aperture 204. In one or more embodiments, optic fiber shield 810 may be configured to prevent instrument tip 1110 from damaging a portion of optic fiber 600 during an initial insertion 1100. FIG. 11B illustrates a complete insertion 1101. In one or more embodiments, a surgeon may perform a complete insertion 1101 by actuating instrument tip 1110 through hub aperture 204 and causing instrument tip 1110 to ingress valve 400. Illustratively, a surgeon may perform a complete insertion 1101 by actuating instrument tip 1110 through valve 400 and causing instrument tip to egress valve 400. In one or more embodiments, a surgeon may perform a complete insertion 1101 by actuating instrument tip 1110 through valve 400 and causing instrument tip 1110 to ingress cannula base 300. Illustratively, a surgeon may perform a complete insertion 1101 by actuating instrument tip 1110 through cannula base 300 and causing instrument tip 1110 to ingress illumination tube 100. In one or more embodiments, a surgeon may perform a complete insertion 1101 by actuating instrument tip 1110 through illumination tube 100 and causing instrument tip 1110 to egress illumination tube 100. Illustratively, hub 200 may be manufactured from a material configured to minimize resistance to movements of hypodermic tube 1120, e.g., hub 200 may be manufactured from silicone.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a cannula, the teachings of the present invention are equally suitable to any systems where the functionality may be employed. Therefore, it is the object of the appended claims to cover all such variations and modifications as come within the true spirit and scope of the invention.

What is claimed is:

1. A cannula comprising:
   a hub having a hub distal end and a hub proximal end;
   a hub inner lumen of the hub;
   a cannula base having a cannula base distal end and a cannula base proximal end, the cannula base fixed to a portion of the hub;
   a valve having a valve distal end and a valve proximal end, the valve disposed in the cannula base;
   an illumination tube having an illumination tube distal end and an illumination tube proximal end wherein the illumination tube proximal end is disposed in the cannula base;
   an optic fiber guide having an optic fiber guide distal end and an optic fiber guide proximal end, the optic fiber guide disposed in the hub inner lumen;
   an illumination source connector having an illumination source connector distal end and an illumination source connector proximal end;
   an optic fiber having an optic fiber distal end and an optic fiber proximal end, the optic fiber disposed in the illumination source connector, the hub inner lumen, the optic fiber guide, and the cannula base; and
   an optic fiber lumen of the cannula base having an optic fiber lumen distal end and an optic fiber lumen proximal end wherein the optic fiber is disposed in the optic fiber lumen; and
   a tapered portion of the optic fiber lumen configured to guide the optic fiber distal end out from the optic fiber lumen distal end wherein the optic fiber distal end is disposed flush with the illumination tube proximal end.

2. The cannula of claim 1 further comprising:
   an anterior lip of the cannula base having an anterior lip distal end and an anterior lip proximal end.

3. The cannula of claim 2 further comprising:
   a posterior lip of the cannula base having a posterior lip distal end and a posterior lip proximal end.

4. The cannula of claim 1 further comprising:
   a sclera interface of the cannula base having a sclera interface distal end and a sclera interface proximal end.

5. The cannula of claim 1 further comprising:
   an optic fiber shield of the optic fiber guide wherein the optic fiber is disposed in the optic fiber shield.

6. The cannula of claim 5 further comprising:
   a hub aperture at the hub distal end of the hub.

7. The cannula of claim 6 wherein the optic fiber shield is configured to dispose the optic fiber inferior to the hub aperture.

8. The cannula of claim 6 wherein the optic fiber shield is configured to dispose the optic fiber superior to the hub aperture.

9. The cannula of claim 1 wherein the optic fiber is manufactured from silica.

10. The cannula of claim 1 wherein the illumination tube is manufactured from silica.

11. The cannula of claim 1 further comprising:
    an optic fiber housing of the illumination source connector.

12. The cannula of claim 1 further comprising:
    a connector base of the illumination source connector.

13. A cannula comprising:
    a hub having a hub distal end and a hub proximal end;
    a hub inner lumen of the hub;
    a hub aperture at the hub distal end of the hub;
    a cannula base having a cannula base distal end and a cannula base proximal end, the cannula base fixed to a portion of the hub;
    an anterior lip of the cannula base having an anterior lip distal end and an anterior lip proximal end;
    a posterior lip of the cannula base having a posterior lip distal end and a posterior lip proximal end;
    a valve having a valve distal end and a valve proximal end, the valve disposed in the cannula base;
    an illumination tube having an illumination tube distal end and an illumination tube proximal end wherein the illumination tube proximal end is disposed in the cannula base;
    an optic fiber guide having an optic fiber guide distal end and an optic fiber guide proximal end, the optic fiber guide disposed in the hub inner lumen;
    an illumination source connector having an illumination source connector distal end and an illumination source connector proximal end;
    an optic fiber having an optic fiber distal end and an optic fiber proximal end, the optic fiber disposed in the illumination source connector, the hub inner lumen, the optic fiber guide, and the cannula base;
    an optic fiber lumen of the cannula base having an optic fiber lumen distal end and an optic fiber lumen proximal end wherein the optic fiber is disposed in the optic fiber lumen; and
    a tapered portion of the optic fiber lumen configured to guide the optic fiber distal end out from the optic fiber lumen distal end wherein the optic fiber distal end is disposed flush with the illumination tube proximal end.

14. The cannula of claim 13 further comprising:
    an optic fiber shield of the optic fiber guide wherein the optic fiber is disposed in the optic fiber shield.

15. The cannula of claim 14 wherein the optic fiber shield is configured to dispose the optic fiber inferior to the hub aperture.

16. The cannula of claim 14 wherein the optic fiber shield is configured to dispose the optic fiber superior to the hub aperture.

\* \* \* \* \*